(12) United States Patent
Kim et al.

(10) Patent No.: US 10,478,228 B2
(45) Date of Patent: Nov. 19, 2019

(54) SCREW ASSEMBLY FOR SPINAL IMPLANT

(71) Applicants: Min-na Kim, Seoul (KR); Il-jin Jeon, Seoul (KR)

(72) Inventors: Min-na Kim, Seoul (KR); Il-jin Jeon, Seoul (KR); Chang-hoon Jeon, Seoul (KR)

(*) Notice: Subject to any disclaimer, the term of this patent is extended or adjusted under 35 U.S.C. 154(b) by 0 days.

(21) Appl. No.: 15/316,758

(22) PCT Filed: Nov. 1, 2016

(86) PCT No.: PCT/KR2016/012428
§ 371 (c)(1),
(2) Date: Dec. 6, 2016

(87) PCT Pub. No.: WO2018/084325
PCT Pub. Date: May 11, 2018

(65) Prior Publication Data
US 2019/0247096 A1   Aug. 15, 2019

(51) Int. Cl.
*A61B 17/70* (2006.01)
*A61B 17/86* (2006.01)
(52) U.S. Cl.
CPC ...... *A61B 17/7037* (2013.01); *A61B 17/7032* (2013.01); *A61B 17/8685* (2013.01)
(58) Field of Classification Search
CPC .............. A61B 17/7001; A61B 17/7032–704
See application file for complete search history.

(56) References Cited

U.S. PATENT DOCUMENTS

| | | | | |
|---|---|---|---|---|
| 9,453,526 B2* | 9/2016 | Black | ................. | A61B 17/7037 |
| 9,820,782 B2* | 11/2017 | Daniels | .............. | A61B 17/7032 |
| 9,924,975 B2* | 3/2018 | Jackson | ............. | A61B 17/7037 |
| 2006/0084981 A1* | 4/2006 | Shluzas | .............. | A61B 17/7037 |
| | | | | 606/328 |
| 2008/0015579 A1* | 1/2008 | Whipple | ............ | A61B 17/7037 |
| | | | | 606/250 |
| 2008/0015580 A1* | 1/2008 | Chao | ................... | A61B 17/7037 |
| | | | | 606/86 A |
| 2008/0015597 A1* | 1/2008 | Whipple | ............ | A61B 17/7037 |
| | | | | 606/250 |
| 2008/0183216 A1* | 7/2008 | Jackson | ............... | A61B 17/701 |
| | | | | 606/278 |

(Continued)

FOREIGN PATENT DOCUMENTS

KR    10-0509885    8/2005
KR    10-1056119    8/2011

*Primary Examiner* — Nicholas J Plionis
(74) *Attorney, Agent, or Firm* — Antonio Ha & U.S. Patent, LLC

(57) ABSTRACT

A screw assembly for a spinal implant comprises a first unit including insertion holes and an inner space, a rod having a side whose outer circumference surface is positioned on the insertion holes of the first unit and another side whose outer circumference surface is positioned on insertion holes of another first unit positioned adjacent to the first unit, a second unit having an upper portion rotatably received in a lower portion of the inner space and a lower portion screwed to a vertebral body, a third unit screwed to an upper portion of the inner space to hold the rod, and a fourth unit positioned between the inner space and the upper portion of the second unit and including a pressure cap seated in the inner space.

16 Claims, 13 Drawing Sheets

(56) References Cited

U.S. PATENT DOCUMENTS

2008/0294202 A1* 11/2008 Peterson ............ A61B 17/7032
606/305
2010/0094349 A1* 4/2010 Hammer ............ A61B 17/7034
606/264

* cited by examiner (a)

(b)

(c)

SCREW ASSEMBLY FOR SPINAL IMPLANT

CROSS-REFERENCE TO RELATED APPLICATIONS

This patent application is a national-stage application of International Patent Application No. PCT/KR2016/012428 filed on Nov. 1, 2016, the disclosure of which is incorporated by reference herein in its entirety.

TECHNICAL FIELD

The present invention relates to a screw assembly for a spinal implant and, more specifically, to a screw assembly for a spinal implant capable of applying to various body types of patients, easily adjusting the angle and position for installation thereof, and firmly maintaining a state of a procedure.

DISCUSSION OF RELATED ART

The spine, part of a human body to support, generally consists of 24 bones, with a disc positioned between two adjacent ones thereof and a nerve passing through the spinal canal.

Not only support the human body does the spine also carry out important functions as a fundamental part to move the body.

If one's spine is damaged by an accident or so, suffers from a degressive disease with age, or is injured or twisted, the discs functioning as a shock absorber between the vertebral bodies of the spine are pressurized, so is the nerve, causing a severe pain.

A conservative treatment is intended for a slight pain. To treat a severe pain, however, a spinal fastener should be implanted to rectify the position of the spine or correction is required to release the pressure on the nerve.

The spinal fastener is allowed to insert multiple screws into the pedicle in two adjacent vertebral bodies and install a rod to couple together the screws to fasten the vertebral bodies or correct the deformed spine.

However, such a conventional spinal fastener has the drawback that, as the patient's continuous activity may force the spine to move, the screws fixed to the vertebral bodies may loosen or reversely rotate to escape off.

In this case, the patient needs to take the procedure again, which would not only retard recovery but also take longer to do so. Resultantly, the patient would suffer from more pain.

PRIOR ART DOCUMENT

Patent Document (Patent Document 1) Korean Patent No. 10-0509885
(Patent Document 2) Korean Patent No. 10-1056119

SUMMARY

The present invention addresses the above-described issues to provide a screw assembly for a spinal implant that freely adjusts an angle and position of a procedure or an installation depending on various types of patients and maintains a firm state of the procedure.

In order to achieve the above object, the present invention may provide a screw assembly for a spinal implant comprising a first unit including insertion holes positioned opposite each other, cut from an edge of an upper end of the first unit, and forming an inner space, the first unit penetrated from top to bottom, a rod having a side whose outer circumference surface is positioned on the insertion holes of the first unit and another side whose outer circumference surface is positioned on an insertion holes of another first unit positioned adjacent to the first unit, a second unit having an upper portion rotatably received in a lower portion of the inner space and a lower portion screwed to a vertebral body of a spine not to be released; a third unit screwed to an upper portion of the inner space to hold the rod, a fourth unit positioned between the inner space and the upper portion of the second unit to restrict a rotation of the second unit and including a pressure cap seated in the inner space while pressing an outer surface of an upper portion of a ball joint head disposed on the upper portion of the second, unit and having an upper portion contacting the outer circumference surface of the rod to be pressurized by a coupling force of the third unit coupled with the first unit, and a fifth unit enabling the pressure cap of the fourth unit to be inserted into the first unit and including a C-ring preventing the inserted pressure cap from escaping off.

According to the above configuration of the present invention, the following effects can be achieved.

First, the present invention is configured to include a fourth unit comprising a pressure cap restricting a rotation of an upper portion of a second unit to prevent a lower portion of the second unit to escape from a pedicle due to an external force applied by various actions of a patient and to maintain a sturdy state of a treatment.

Further, a fifth unit including a C-ring prevents the pressure cap inserted into a first unit from loosening or escaping off so that a more sturdy and solid assembly can be maintained.

Further, according to the present invention, the second unit is rotatably connected to the first unit so that treatment and installation angles different according to the age, body type, or extent of disease of a patient can be changed. Thus, the present invention is excellent in light of a wide use.

Moreover, the present invention includes various types of holes, specifically a linear groove for holding, a first hole for holding, and a second notch for holding, in the first unit so that a minimally invasive surgery as well as a general operation is performed while an operational tool firmly clamps the first unit, thereby obtaining an excellent result of a procedure.

DETAILED DESCRIPTION OF EXEMPLARY EMBODIMENTS

Advantages and features of the present invention and methods for achieving the same will be apparent from the following embodiments described below in detail with reference to the accompanying drawings.

However, the present invention will be not limited to the following disclosed embodiments but may be embodied in various forms.

In the present specification, the embodiments are provided to enable the present invention to be fully disclosed and provide one of ordinary skill in the art with a thorough understanding of the scope of the present invention.

Further, the present invention is defined by only the scope of the claims.

Thus, known components, operations, and techniques in some embodiments are excluded from the description in order to avoid an ambiguous interpretation for the present invention.

Further, the same reference number refers to the same component throughout the specification, and the terms used (mentioned) herein are intended for describing the embodiments, not to limit the present invention.

In the present specification, a singular form includes a plural form unless mentioned, otherwise, and a component and an operation mentioned along with the term "comprise (or include)" do not exclude existence or addition of one or more other components and operations.

Unless defined otherwise, all of the terms used herein (including technical and scientific terminology) may be used as meanings commonly appreciated by one of ordinary skill in the art.

Further, words or terms defined in a commonly used dictionary are not ideally or overly construed.

Hereinafter, preferable embodiments of the present invention are described in detail with reference to the accompanying drawings.

Figure 1:
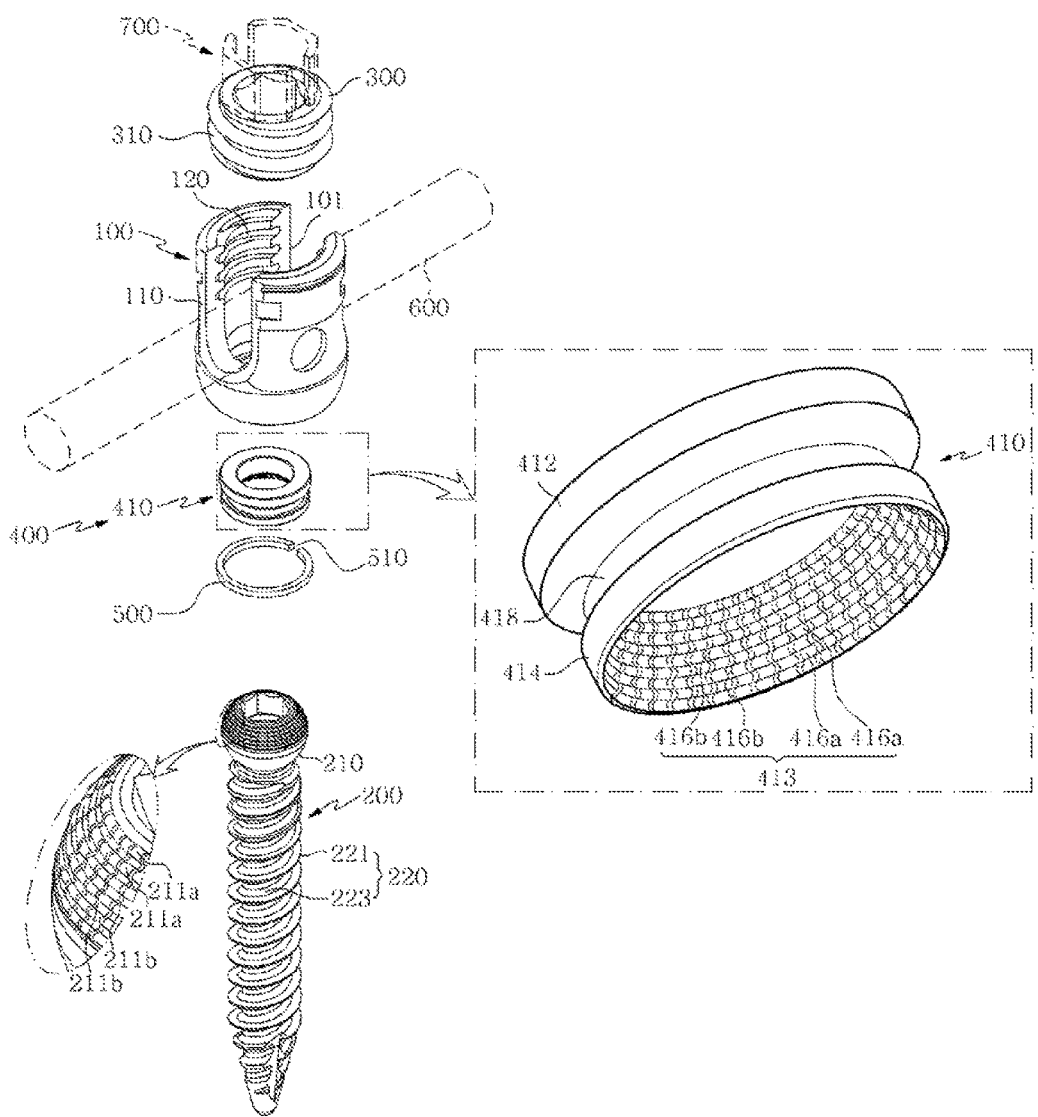
FIG. 1 is an exploded perspective view illustrating a general combination relation of a screw assembly for a spinal implant according to an embodiment of the present invention.
Figure 2:
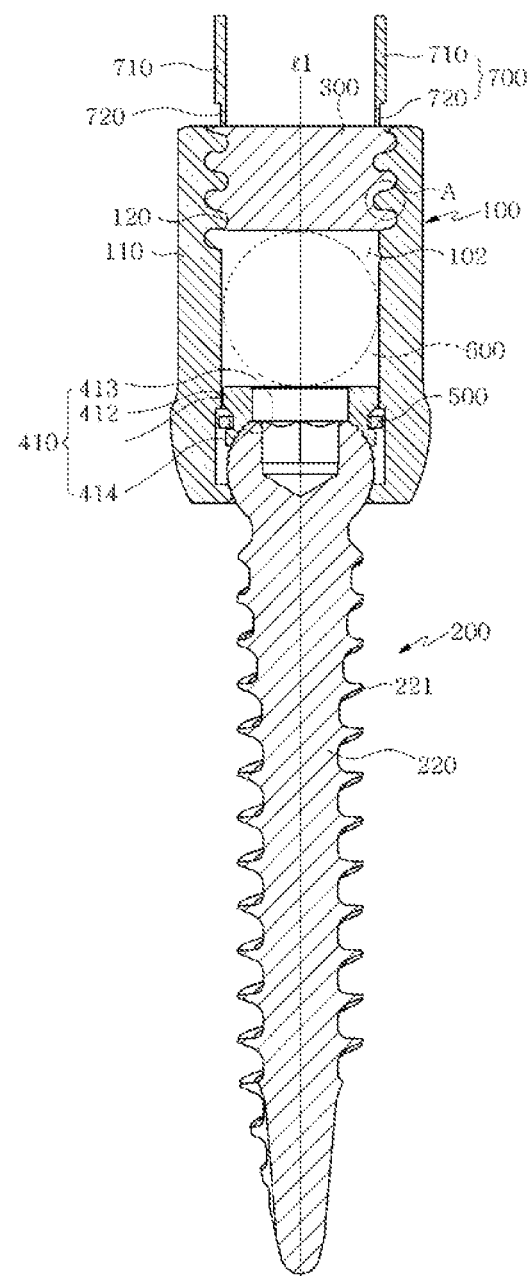
FIG. 2 is a cross-sectional conceptive view illustrating a general combination relation of a screw assembly for a spinal implant according to an embodiment of the present invention.

FIG. 1 is an exploded perspective view illustrating a general combination relation of a screw assembly for a spinal implant according, to an embodiment of the present invention, and FIG. 2 is a cross-sectional conceptive view illustrating a general combination relation of a screw assembly for a spinal implant according to an embodiment of the present invention.

As illustrated in FIGS. 1 and 2, the present invention can be appreciated as a configuration where a rod 600 is positioned in a first unit 100, the rod 600 is fixed by a third 300, an upper portion of a second unit 200 is rotatably inserted in the first unit 100, and a fourth unit 400 limits rotation of the second unit 200 when a procedure is finished to maintain a sturdy state of the procedure.

Here, a fifth unit 500, such as a C-ring 500, described below prevents the fourth unit 400 inserted in the first unit 100 from loosening and escaping off.

The first unit 100 is a member vertically penetrated and including insertion holes 101 positioned opposite each other, cut front the edge of an upper portion of the first unit 100, and having an arc-shaped lower portion and an inner space 102.

An outer circumference surface of a first side of the rod 600 is positioned in the insertion holes 101, and an outer circumference surface of a second side of the rod 600 is positioned in the insertion holes 101 of another first unit 100 positioned adjacent to the first unit 100.

An upper portion of the second unit 200 is rotatably positioned in a lower portion of the inner space 102, and a lower portion of the second unit 200 is stuck and fastened to both sides of each vertebral body pedicle 810 (hereinafter, refer to FIG. 14) included in a spine 800 (hereinafter, refer to FIG. 14).

The third unit 300 is screwed, with an upper portion of the inner space 102 to fix the rod 600.

The fourth unit 400 is positioned between the inner space 102 and an upper portion of the second unit 200 to limit the rotation of the second unit 200.

Here, the fourth unit 400 includes a pressure cap 410 pressing an outer surface of an upper portion of a ball joint head 210 positioned in the upper portion of the second unit 200, positioned in the inner space 102 with the outer circumference surface of the rod 600 contacting an upper portion of the forth unit 400, and pressed by a coupling force of the third unit 300 coupled with the first unit 100.

The fifth unit 500, which is a C-ring 500 described below, is positioned on a receiving groove 418 formed in an outer surface of the pressure cap 410 of the fourth unit 400 to prevent the fourth unit 400 from loosening or escaping from the first unit 100 after the fourth unit 400 has been inserted into the first unit 100.

Thus, the present invention can keep the interval between two adjacent first pedicles 810 at such an extent as to relieve pain due to pressure on the nerve.

In other words, the first unit 100 and another first unit 100 are provided, the second units 200 respectively positioned in the first units 100 are inserted and fastened in the pedicle 810, and the rod 600 maintains a distance between the two adjacent first units 100.

Not only the above-described embodiments of the present invention but other various embodiments that follow may apply as well.

As described above, the first unit 100 receives the rod 600, including a housing 110 and a second screw part 120.

The housing 110 includes the insertions holes 101 extending from its upper edge and positioned opposite each other and the inner space 120.

The second screw part 120 is formed along an inner circumference surface of an upper portion of the housing 110 to couple with a rounded screw-shaped first screw pan 310 formed in an outer circumference surface of the third unit 300. A valley formed between two neighboring ridges of the screw thread formed in the first screw part 310 has a rounded shape.

Meanwhile, the third unit 300 may further comprise a pair of supports 700 (refer to FIG. 1) positioned opposite each other and extending from an upper portion of the third unit 300.

In order to couple and fasten the second unit 200 combined with the first unit 100 to the spine 800, the operator places the third unit 300 at a desired position on the patient's spine 800, with the third unit 300 fixed onto one end of an operational tool (not shown).

The supports 700 prevent the third unit 300 from escaping from the operational tool to fall onto the patient's operational portion due to the operator's carelessness during the operation.

In order for the operator to eliminate the unnecessary supports 700 after coupling and fastening a screw nail onto the spine 800, a lower portion of each support 700 is formed thin to be easily cut.

In other words, the supports 700 extend from an upper portion of the third unit 300, are tightly contacted and fastened onto the operational tool and are eliminated after the third unit 300 is coupled by the operational tool, and the supports 700 can be a technical means to provide working convenience to the operator.

Figure 3:
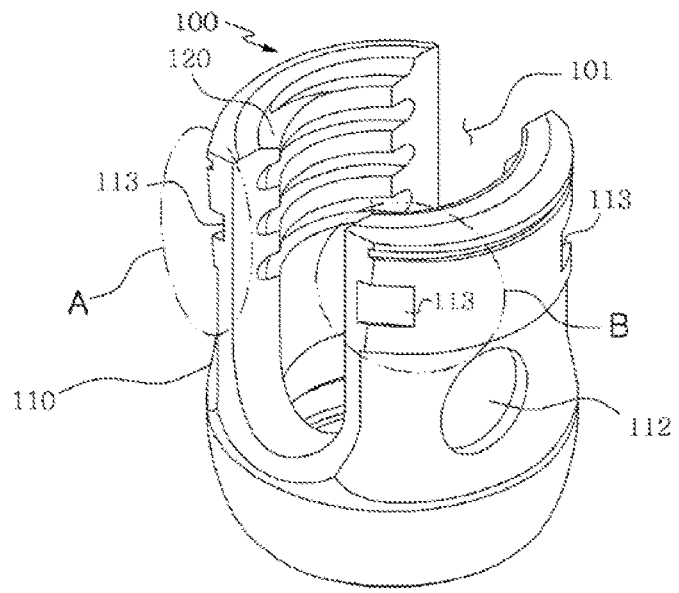
FIG. 3 is an external perspective view illustrating a first unit as a main part of a screw assembly for a spinal implant according to an embodiment of the present invention.
Figure 5:
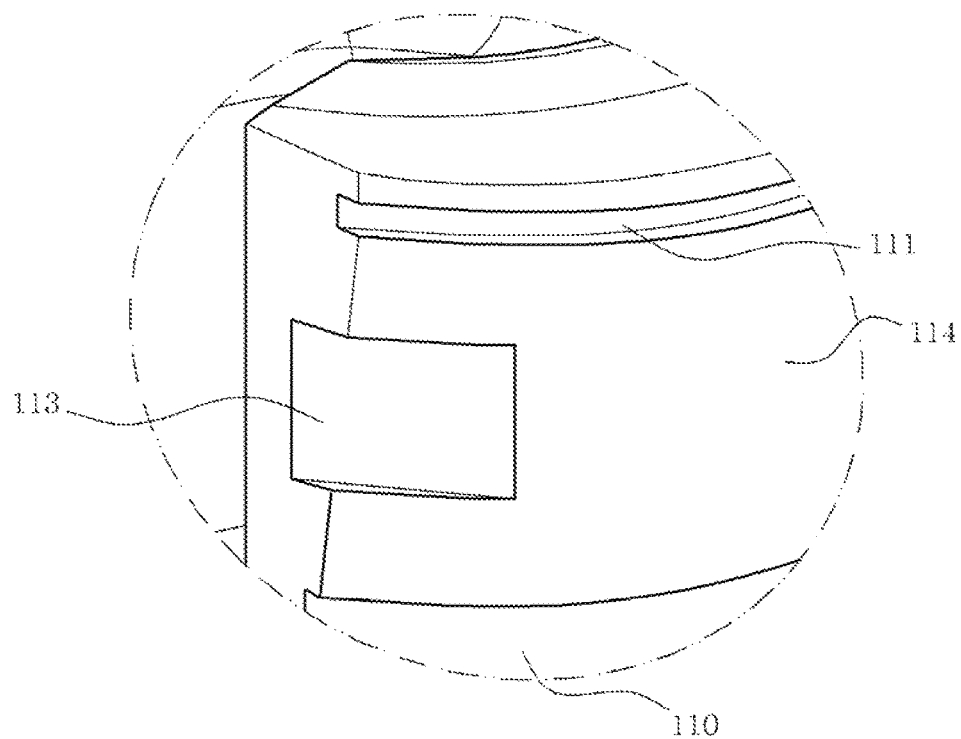
FIG. 5 is an enlarged perspective view of a portion B of the FIG. 3.

Meanwhile, as illustrated in FIGS. 3 and 5, the first unit 100 can be configured to further comprise a linear groove 111 for holding, depressed in parallel with an upper surface of the first unit 100 along an outer surface of the upper portion of the first unit 100, a first hole 112 for holding, depressed into a preset depth and size in the outer surface of the first unit 100 and positioned in a lower portion of the linear groove 111, and a rectangular second notches 113 for holding, positioned between the linear groove 111 and first hole 112 and depressed at both edges of each of the insertion holes 101 positioned opposite each other to be arrayed along an outer surface of the first unit 100.

Herein, the above-described linear groove 111, the first hole 112, and the second notches 113 enable a procedure to be performed, with the operational tool (not shown) securely clamped with the first unit 100, allowing the procedure an excellent result.

Figure 4:
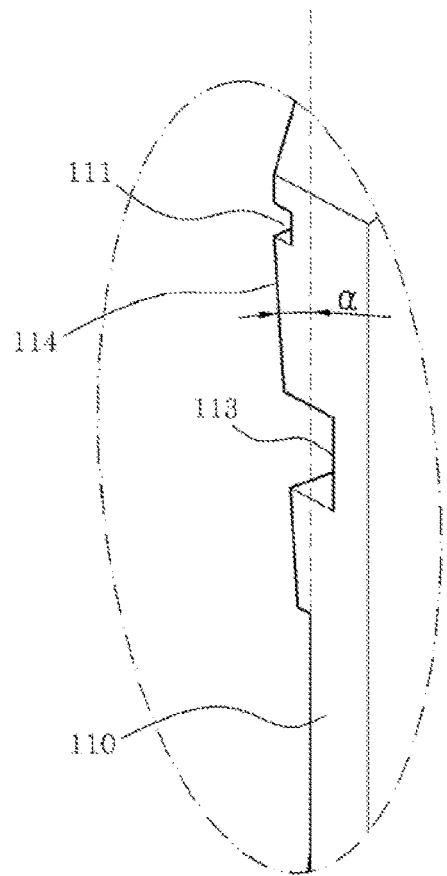
FIG. 4 is an enlarged perspective view of a portion A of the FIG. 3.

As illustrated in FIGS. 3 and 4, the first unit 100 preferably further comprises a slanted part 114, as a predetermined portion of the outer surface of the first unit 100, that gradually broadens to an edge of an upper surface of the first unit 100.

The slanted part 114 enables a minimally invasive surgery as well as a general operation to be performed while an operational tool firmly clamps the first unit 100 and may be a technical means for preventing the first unit 100, i.e., the housing 110 from escaping off the operational tool.

To this end, an angle α between the slanted part 114 and the outer surface of the first unit 100 preferably ranges from 0.1 degrees to degrees. When the angle is 0.1 degrees or, less, the housing 110 may escape from the operational tool. When the angle is 5 degrees or more, it may be difficult for the operational tool to clamp the first unit 100.

In other words, if the angle is 5 degrees or less, there is no concern that the housing 110 will escape from the operational tool.

Figure 6:
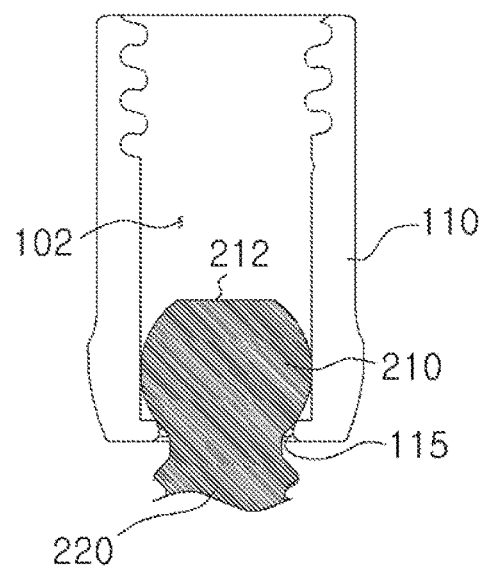
FIGS. 6 and 7 illustrate a variety of modified examples of cross-sectional views describing states of coupling a second unit with a first unit before fixing by a fourth unit or a fifth unit when combining a screw assembly for a spinal implant according to an embodiment of the present invention.

Meanwhile, as illustrated in FIG. 6, the second unit 200 comprises a ball head joint 210 received in the inner space 102 and seated in the first unit 100 and a coupler 220 with a screw thread 221, extending from a lower portion of the ball joint head 210 and exposed through a through-hole 115 passing through a bottom surface of the first unit 100 to communicate with the inner space 102 and inserted and fastened to the pedicle 810.

Here, a diameter of the through-hole 115 is formed to be greater or smaller than a diameter of the coupler 220, and a diameter of the ball joint head 210 is formed to be greater than the diameter of the through-hole 115 so that the ball joint head 210 can smoothly rotate within the housing 110 during a procedure.

Figure 7:
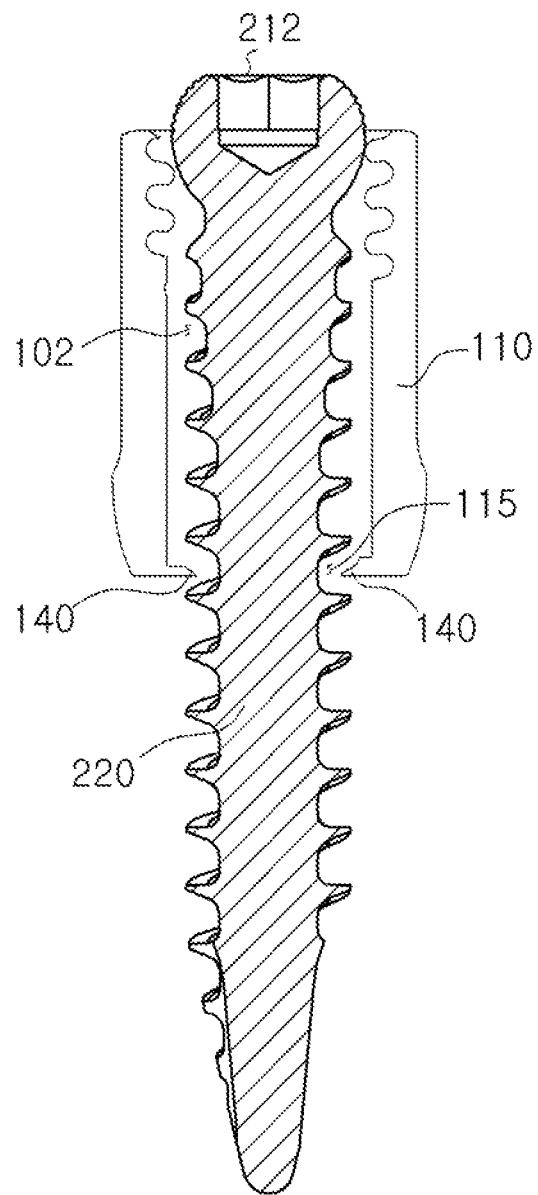

Here, as an alternative to the embodiment illustrated in FIG. 6, a first provisional coupling screw thread 140 may be further formed along an inner circumference surface of the through-hole 115 so that the to ball joint head 210 can smoothly rotate within the housing 110, as shown in FIG. 7.

That is, the embodiment illustrated in FIG. 6 is configured so that the coupler 220 is inserted into the housing 110, as it is, through a top of the housing 110. On the other hand, as per the embodiment illustrated in FIG. 7, when the coupler 220 is screw-rotated, the screw thread 221 formed along a direction of formation of the coupler 220 is also rotated along the first provisional coupling screw thread 140 formed in the housing 110 as if a male screw and a female screw are mutually coupled, so that the overall coupler 220 can be inserted into the housing 110.

Figure 8:
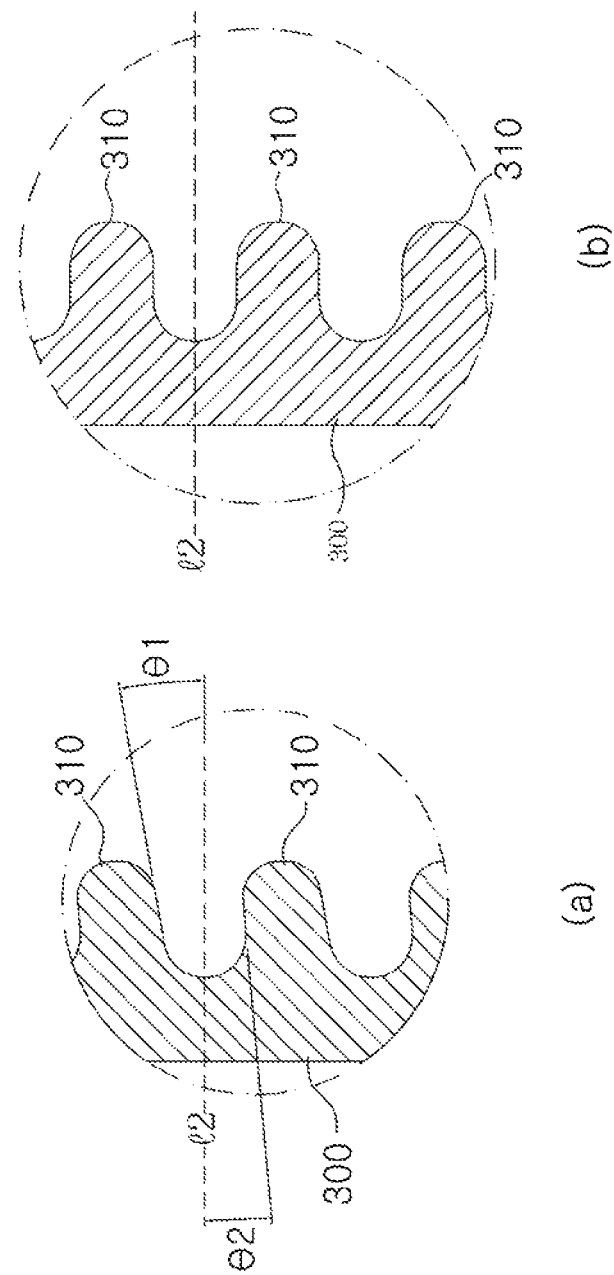
FIGS. 8 and 9 are partial enlarged cross-sectional conceptive views schematically illustrating formative direction and arrangement configuration of a screw thread for a third unit as a main part of a screw assembly for a spinal implant according to an embodiment of the present invention.

Meanwhile, referring back to FIG. 1 along with FIG. 8, the present invention may comprise the rounded screw-shaped first screw part 310 formed in an outer circumference surface of the third unit 300 and the rounded screw-shaped second screw part 120 formed along an inner circumference surface of an upper portion of the inner space 102 of the first unit 100 and coupling with the first screw part 310.

Figure 12:
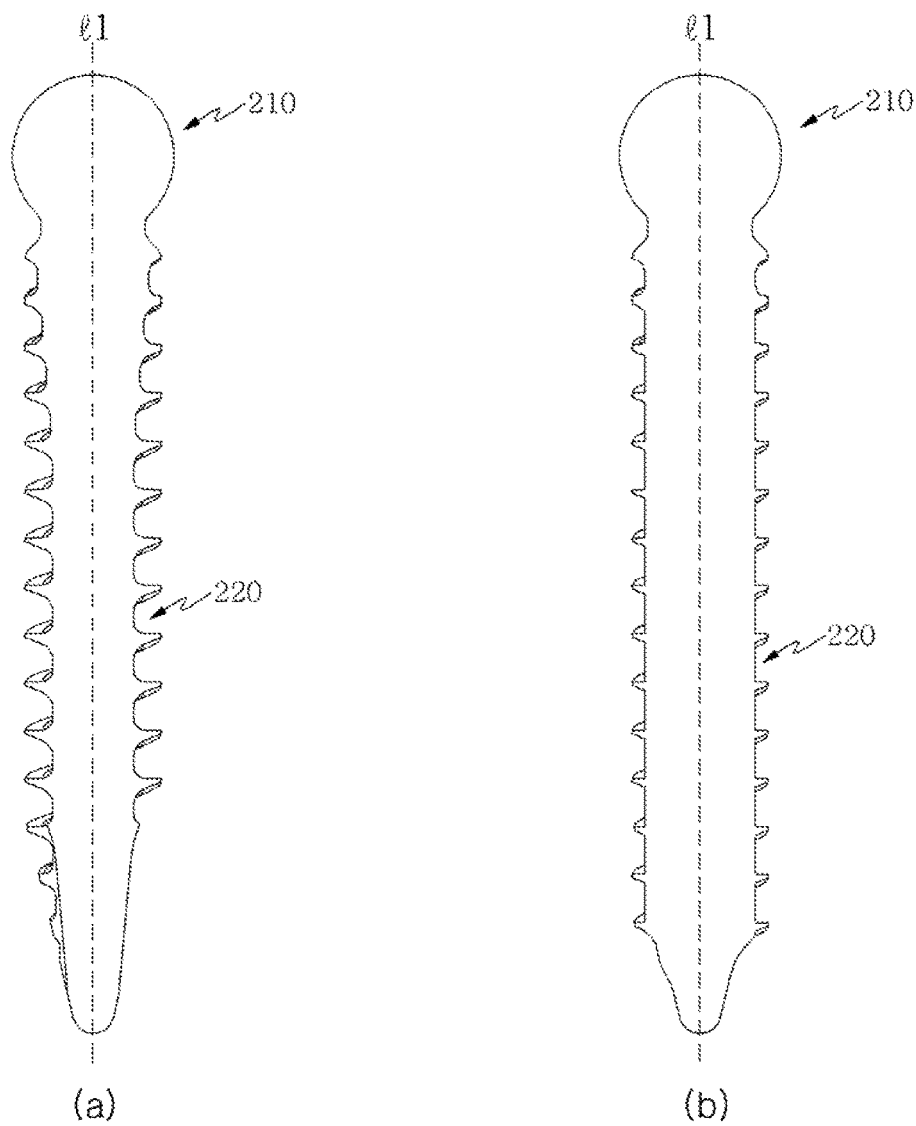
FIG. 12 is cross-sectional view illustrating a second unit of a screw assembly for a spinal implant according to embodiments of the present invention.

In other words, as illustrated in FIG. 8a, the rounded screw-shaped screw thread 221 included in each of the first screw part 310 and the second screw part 120 is formed to be inclined upward with respect to a first virtual line l1 (hereinafter, refer to FIG. 12) passing through the center of a first unit 400 along an upper-lower longitudinal direction of the first unit 100.

In other words, it may be a technical means to allow the first screw part 310 to be precisely and easily guided and rotatably pushed into the second screw part 120 of the first unit 100.

More specifically, a first inclined angle θ1 between a second virtual line l2, passing through a center of a screw thread of the first screw part 310 or the second screw part 120 and perpendicular to the first virtual line l1, and a screw thread of an upper portion of the second virtual line l2 is preferably the same or different from a second inclined angle θ2 between the second virtual line l2 and a screw thread of a lower portion of the second virtual line l2.

The configuration of the first, screw part 310 and the second screw part 120 allows the third unit 300 securely coupled to the first unit 100 to tightly contact and further pressurize the first unit 100 and the third unit 300 to be easily inserted into, the first unit 100.

Figure 9:
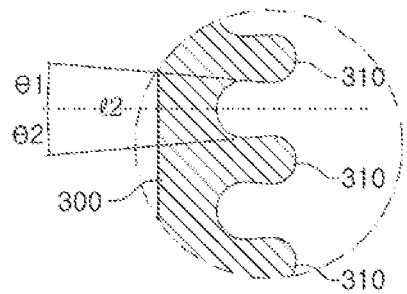
Figure 9:
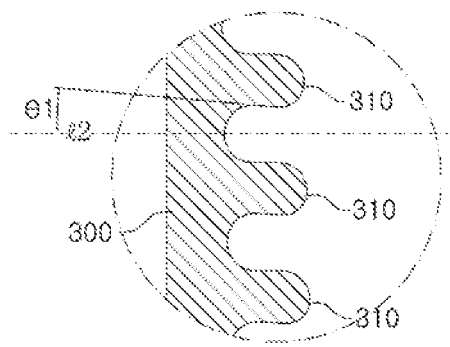
Figure 9:
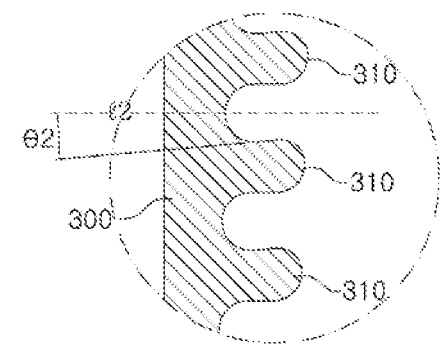

Further, as illustrated in FIG. 8b, according to the present invention, the rounded screw-shaped screw thread 221 included in each of the first screw part 310 and a second screw part 120 may be formed to be perpendicular to the first virtual line l1 passing through the center of the first unit 100 along an upper-lower longitudinal direction of the first unit 100, which is also applicable to embodiments as illustrated in FIG. 9.

In other words, as illustrated in FIG. 9a, according to the present invention, an upper surface of the rounded screw-shaped screw thread included in each of the first screw part 310 and the second screw part 120 may be formed to be inclined upward with respect to the first virtual line 11 passing through the center of the first unit 100 along an upper-lower longitudinal direction of the first unit 100, and a lower surface of each screw thread may be formed to be inclined downward with respect to the first virtual line 11.

Further, as illustrated in FIG. 9b, according to the present invention, an upper surface of the rounded screw-shaped screw thread included in each of the first screw part 310 and the second screw part 120 may be formed to be perpendicular to the first virtual line 11 passing through the center of the first unit 100 along an upper-lower longitudinal direction of the first unit 100, and a lower surface of the screw thread may be formed to be inclined downward with respect to the first virtual line 11.

Moreover, as illustrated in FIG. 9c, according to the present invention, an upper surface of the rounded screw-shaped screw thread included in each of the first screw part 310 and the second screw part 120 may be formed to be inclined upward with respect to the first virtual line 11 passing through the center of the first unit 100 along an upper-lower longitudinal direction of the first unit 100, and a lower surface of the screw thread may be formed to be perpendicular to the first virtual line 11.

Figure 10:
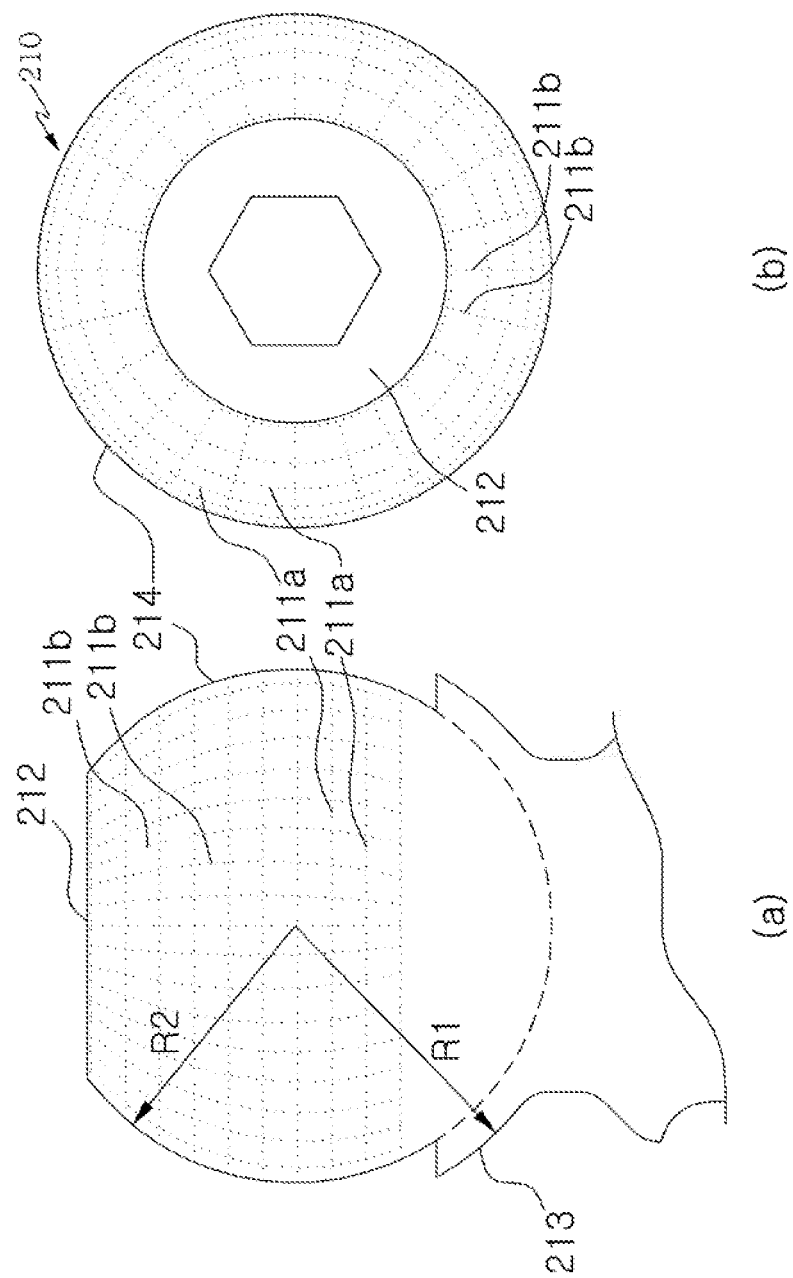
FIG. 10 is a conceptive view illustrating a ball joint head of a second unit as a main part of a screw assembly for a spinal implant according to other embodiment of the present invention.

Meanwhile, as illustrated in an expanded part of FIG. 1 and FIG. 10, the ball joint head 210 can be configured to further comprise a circular flat surface 212, obtained by flatly cutting an upper part thereof, a first horizontal bumping pattern 211a having repetitive ring-shaped bumps concentric from the flat surface 212 to a lower part of the ball joint head 210, and a grid-shaped first vertical bumping pattern 211b having repetitive bumps both ends of each of which are connected to an edge of the flat surface 212 and a lower end of the ball joint head 210 to be perpendicular to the first horizontal bumping pattern 211a.

Here, the first horizontal bumping pattern 211a and first vertical bumping pattern 211b are coupled with the fourth unit 400 to clearly restrict a rotation of the ball joint head 210.

More specifically, as shown in FIG. 10, the ball joint head 210 is configured to comprise a rotational part 214 positioned on a supporting part 213.

The supporting part 213 is a bowl-shaped portion of a sphere having a first radius R1 from the center thereof and the whole or part of a lower surface of the supporting part 213 is seated on the first unit 100, thereby forming a coupler 220 from the lower surface.

The rotational part 214 has the same center as the supporting part 213 and constitutes a portion of a sphere having a second radius R2 smaller than the first radius R1 from the center thereof.

Therefore, since, in the rotational part 214, the spheres having different radii are combined together, the radius of rotation of the second unit 200 is increased, and when the fourth unit 400 presses the second unit 200, the state of a rotational movement of the second unit 200 being stopped becomes more secure, and the rotational part 214 contacts and abuts the center of an upper surface of the supporting part 213, and it, together with the supporting part 213, is rendered to form a single body.

More specifically, the ball joint head 210 comprises the circular flat surface 212 obtained by flatly cutting an upper portion of the sphere-shaped rotational part 214 and further comprises the first horizontal bumping pattern 211a having repetitive ring-shaped bumps having the same center from the flat surface 212 towards a lower part of the rotational part 214.

Further, the ball joint head 210 comprises the grid-shaped first vertical bumping pattern 211b having repetitive bumps both ends of each of which are connected to an edge of the flat surface 212 and a lower end of the rotational part 214 to be perpendicular to the first horizontal bumping pattern 211a.

Therefore, the first horizontal bumping pattern 211a and the first vertical bumping pattern 211b are coupled with the fourth unit 400, more securely restricting a rotation of the rotational part 214.

Meanwhile, as illustrated in an expanded view of FIG. 1, a pressure cap 410 is generally configured to include a cap contacting part 412, a cap lower part 414, a first horizontal bumping pattern 416a, a second vertical bumping pattern 416b, and a C-ring 500 receiving groove 418.

In other words, the cap contacting part 412 is a cap-shaped member penetrated in an upper and lower direction and having an outer circumference surface contacting and secured to an inner circumference surface of the first unit 100 forming the inner space 120.

The cap lower part 414 extends downwards along an edge of a lower portion of the cap contacting part 412 and comprises a pressing groove 413 inside a bottom of the cap lower part 414, which is shaped to correspond to an outer surface of an upper portion of the ball joint head 210.

A plurality of second horizontal bumping patterns 416a are formed along a direction of forming the pressing groove 413, corresponding to the first horizontal bumping pattern 211a having repetitive ring-shaped bumps concentric from the center of an upper end of the ball joint head 210 to a lower end thereof.

The second vertical bumping pattern 416b includes repetitive straight line-shaped bumps to form a grid shape to be perpendicular to the second horizontal bumping pattern 416a in the pressing groove 413 of the cap lower part 414.

The receiving groove 418 is formed on an outer surface between the cap contacting part 412 and the cap lower part 414, and a fifth unit 500 which is a C-ring 500 is mounted on the receiving groove 418.

Therefore, the C-ring 500 is mounted on the receiving groove 418 formed on the outer surface between the cap contacting part 412 and the cap lower part 414 and has a cutout part 510, which is obtained by cutting out a portion of a ring-shaped member, to have a contraction force.

In other words, the C-ring 500 enables an easier insertion of the pressure cap 410 into the first unit 100, and plays a role, to prevent the pressure cap 410 inserted into the first unit 100 from escaping off the first unit 100.

Such a configuration of the pressure cap 410 can prevent a bottom side of the second unit 200 from escaping off the pedicle against an external force that occurs due to the patient's actions and firmly maintain the state of the procedure.

Figure 11:
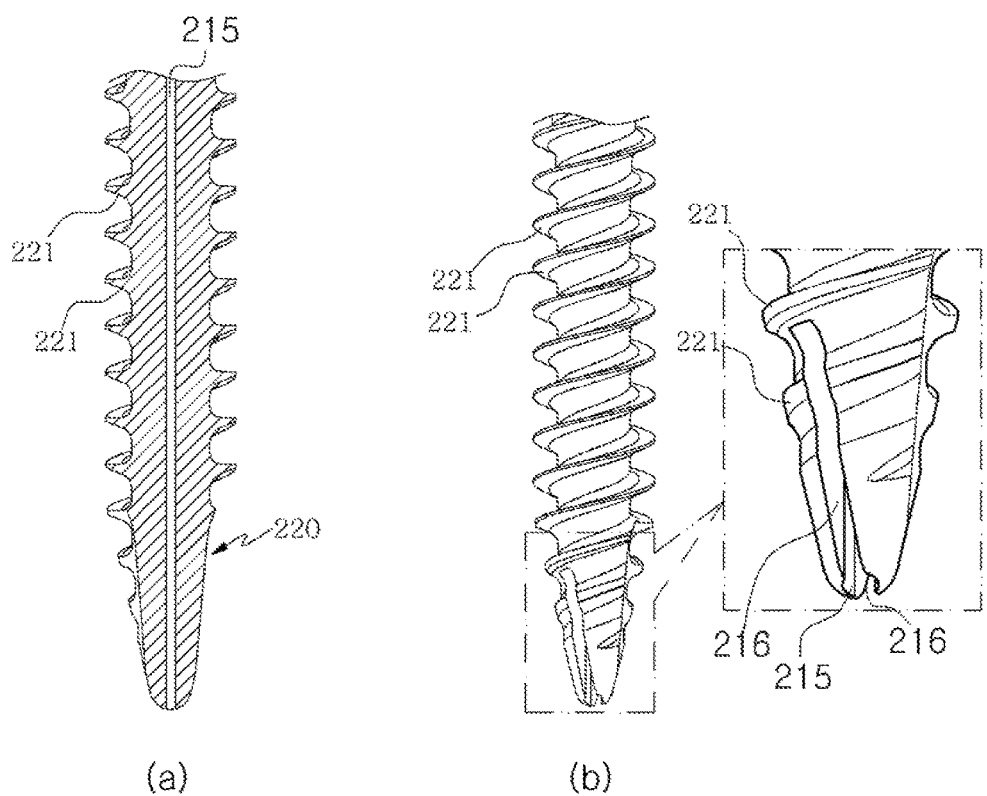
FIG. 11 is a conceptive view illustrating a coupler of a second unit as a main part of a screw assembly for a spinal implant according to other embodiment of the present invention.

Meanwhile, as illustrated in FIG. 11, the second unit 200 further comprises a wire guide path 215 having a predetermined diameter and linearly passing through the center of each of the ball joint head 210 and the coupler 220.

Thus, an operator can put a medical wire (not shown), a bone cement, a bone substitute, or a bone powder for conglutination through, the wire guide path 215.

Here, as illustrated in FIG. 11, the second unit 200 can further comprise one or more cutout slots 216 formed from an end of the coupler 220 to the ball joint head 210 to communicate with the wire guide path 215.

Here, although the cutout slots 216 illustrated in FIG. 11 are shown to be provided in pair, the present invention is not limited thereto and may be modified in design to have a plurality of cutout slots 216.

Here, the cutout slots 216 are a technical means to unfirmly, certainly, and widely distribute a bone cement, a bone substitute, or a bone powder in the patient's vertebral body, as a portion under the procedure.

Meanwhile, the coupler 220 is formed in a tapered shape to narrow from the ball joint head 210 side to an end of the coupler 220, as illustrated in FIG. 12a, or the coupler 220 is formed with a constant diameter from the ball joint head 210 side to an end of the coupler 220, as illustrated in FIG. 12b. Thus, the shape of the coupler 220 may be selected from a tapered shape or a shape with a constant diameter depending on the procedural condition.

Figure 13:
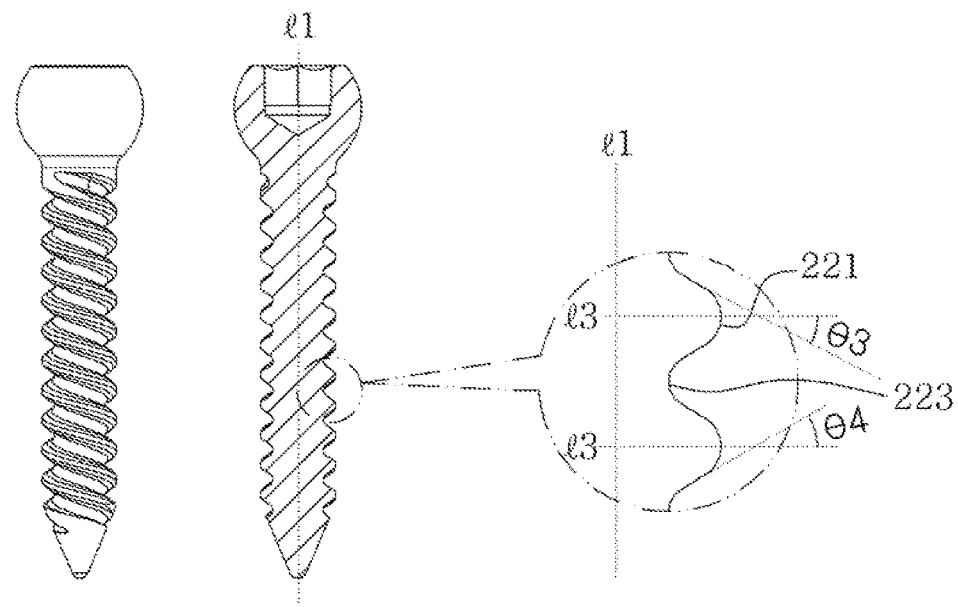
FIGS. 13, 14, 15, and 16 are front views illustrating examples of a second unit of a screw assembly for a spinal implant according to various embodiments of the present invention, wherein the second unit has various screw shapes.
Figure 14:
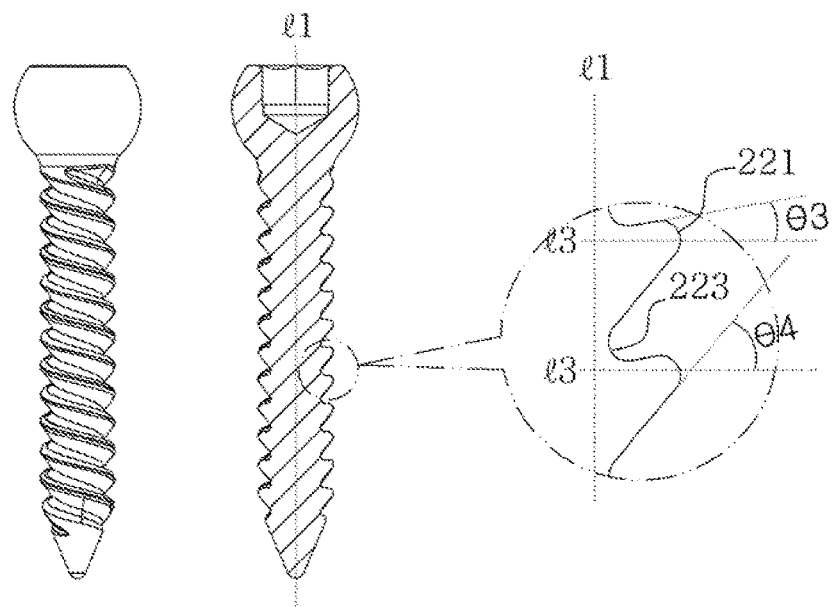
Figure 15:
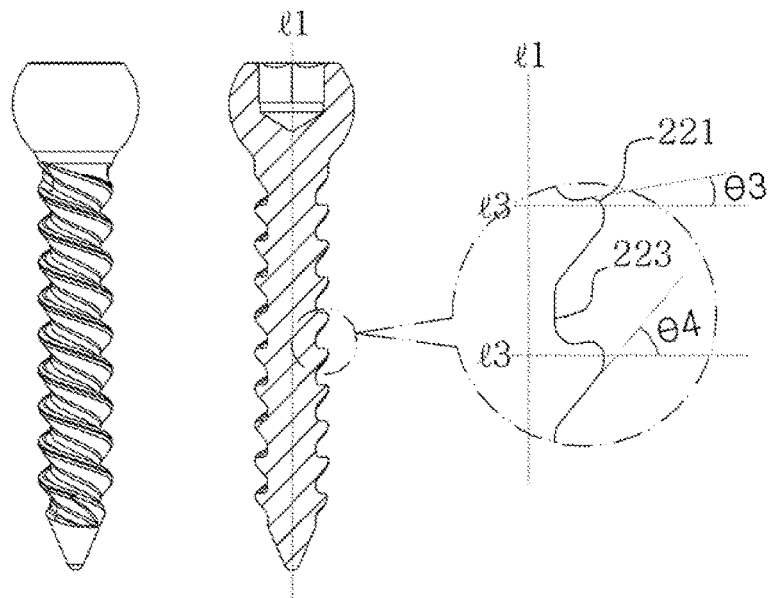

Meanwhile, as illustrated in FIGS. 13, 14, and 15, the coupler 220 includes rounded screw-shaped screw threads 221, is configured that an upper surface of each screw thread 221 is inclined upward or downward with respect to a third virtual line l3 perpendicular to the first virtual line l1 passing through a center of the coupler 220 along an upper-lower longitudinal direction of a second unit 200 or a lower surface of each screw thread 221 is inclined upward with respect to the third virtual line l3 perpendicular to the first virtual line l1, or the embodiments illustrated in FIGS. 13a, 14b, and 13e may be applicable thereto.

More specifically, for the third virtual line l3 passing through a center of a valley between the screw threads 221 and perpendicular to the first virtual line l1, a third angle θ3 of inclination between the third virtual line l2 and a screw thread of an upper portion of the third virtual line l3 is preferably the same or different from a fourth angle θ4 between the third virtual line l3 and a screw thread of a lower portion of the third virtual line l3.

In other words, as illustrated in FIG. 13a, the present invention can be configured so that each upper surface of the screw thread 221 having a rounded screw shape and included in the screw part 221 and 223 is declined downward with respect to the third virtual line l3 perpendicular to the first virtual line l1 passing through a center of the second unit along an upper-lower longitudinal direction of the second unit 200, and each lower surface of the screw thread 221 is inclined upward with respect to the third virtual line l3.

Further, as illustrated in FIG. 14, the present invention can be configured so that each upper surface of the screw thread 221 having a rounded screw shape and included in the screw part 221 and 223 is inclined upward with respect to the third virtual line l3 perpendicular to the first virtual line l1 passing through a center of the second unit along an upper-lower longitudinal direction of the second unit 200, and each lower surface of the screw thread 221 is inclined upward with respect to the third virtual line l3.

Moreover, as illustrated in FIG. 15, the present invention can be configured so that each upper surface of the screw thread 221 having a rounded screw shape and included in the screw part 221 and 223 is inclined upward with respect to the third virtual line l3 perpendicular to the first virtual line l1 passing through a center of the second unit along an upper-lower longitudinal direction of the second unit 200, each lower side of the screw thread 221 is inclined upward with respect to the third virtual line l3, and a shape of the valley 223 between the screw threads 221 is different from a round-shape such the screw part (FIGS. 13, and 14) or each screw part is spaced apart with a preset distance from each other so that the valley 223 may be configured to have a straight line or slight rounded shape.

Figure 16:
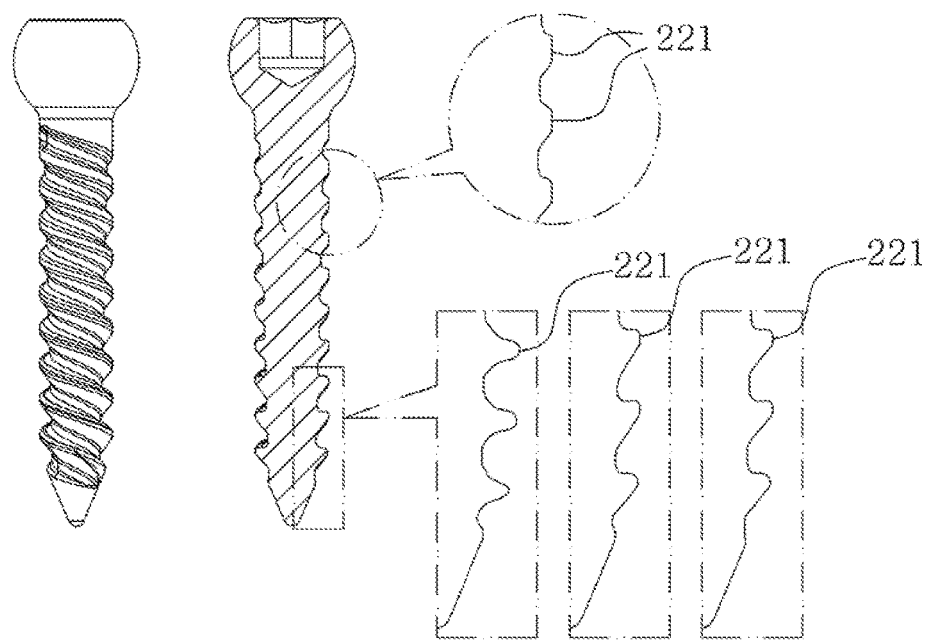
Figure 17:
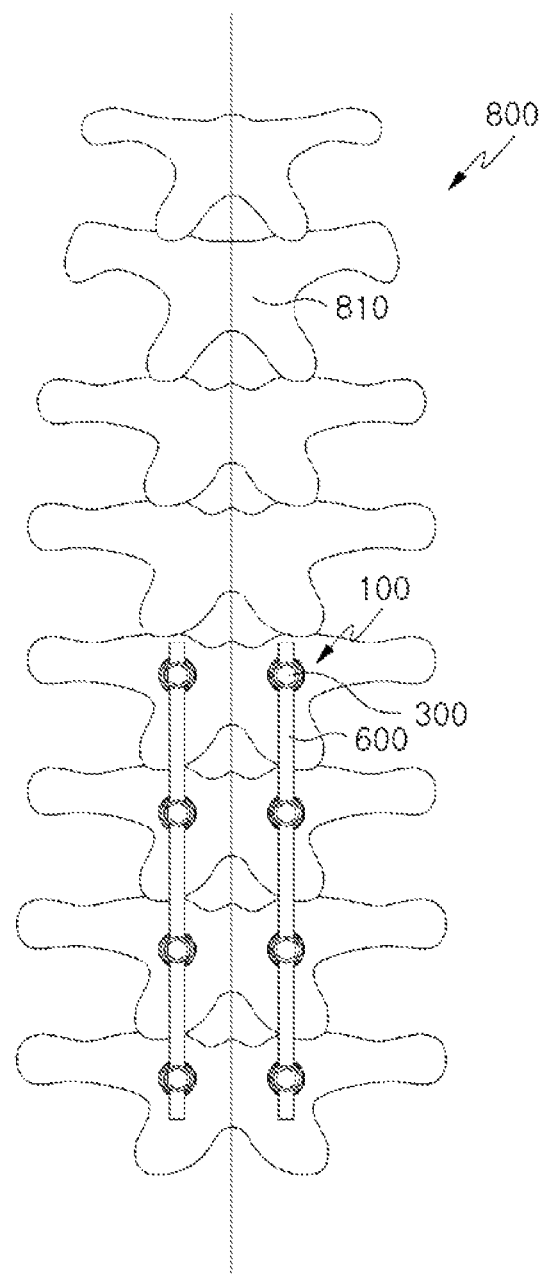
FIG. 17 is a conceptive view illustrating a state in which a screw assembly for a spinal implant according to an embodiment of the present invention is installed in a spine.

Furthermore, as illustrated in FIG. 16, since a distal part of a coupler 220 of a second unit 200 has rounded screw-shaped screw threads, and a proximal part of the coupler 220 has not rounded screw-shaped screw threads, the present invention is configured so that the screw thread 221 of the second unit 200 has rounded screw-shaped screw threads only for a portion of the screw part.

As above-descriptions, it can be known that the present invention has a basic technical concept providing a screw assembly for a spinal implant freely adjusting an angle and a position of a procedure or an installation depending on various body type of a patient and maintaining firm state of the procedure.

Further, it should be appreciated by one of ordinary skill in the art that various changes or derivations may be made thereto within the scope of the basic technical concept of the present invention.

What is claimed is:

1. A screw assembly for a spinal implant, comprising:
 a first unit including insertion holes positioned opposite each other, cut from an edge of an upper end of the first unit, the first unit forming an inner space, and the first unit penetrated from top to bottom, wherein the first unit further comprises:
 a linear groove depressed in parallel with an upper portion of the first unit along an outer circumference surface of the first unit;
 a first hole depressed into a preset depth and a preset size in the outer circumference surface of the first unit to be positioned in a lower portion of the first unit; and
 second holes, having a rectangular shape, positioned between the linear groove and the first hole, and depressed from both edges of each of the insertion holes positioned opposite each other to be disposed along an outer surface of the first unit;
 a rod having a side whose outer circumference surface is positioned on the insertion holes of the first unit and another side whose outer circumference surface is positioned on insertion holes of another first unit positioned adjacent to the first unit;
 a second unit having an upper portion rotatably received in a lower portion of the inner space and a lower portion configured to be screwed into a vertebral body of a spine so s not to be released from the spine;
 a third unit screwed to an upper portion of the inner space to hold the rod;
 a fourth unit positioned between the inner space and the upper portion of the second unit to restrict a rotation of the second unit and including a pressure cap seated in the inner space while pressing an outer surface of an upper portion of a ball joint head disposed on the upper portion of the second unit and having an upper portion contacting the outer circumference surface of the rod to be pressurized by a coupling force of the third unit coupled with the first unit; and
 a fifth unit enabling the pressure cap of the fourth unit to be inserted into the first unit and including a C-ring preventing the inserted pressure cap from escaping off.

2. The screw assembly for a spinal implant of claim 1, wherein the fifth unit including the C-ring is positioned on a receiving groove formed on an outside of the pressure cap of the fourth unit, prevents the fourth unit from loosening or escaping off the first unit with the fourth unit inserted in the first unit, and has a force of contraction.

3. The screw assembly for a spinal implant of claim 1, wherein the first unit further comprises a slanted part formed to gradually broaden from a predetermined portion of an outer surface of the first unit to an edge of an upper surface of the first unit.

4. The screw assembly for a spinal implant of claim 3, wherein an angle between the slanted part and the outer surface of the first unit is 0.5 degrees to 5 degrees.

5. The screw assembly for a spinal implant of claim 1, wherein the second unit comprises the ball joint head received in the inner space and seated in the first unit and a coupler having a screw thread, the coupler extending from a lower side of the ball joint head and passing through a bottom surface of the first unit, the coupler exposed from a through-hole communicating with the inner space, and the coupler inserted and fastened to the vertebral body,
wherein a diameter of the through-hole is greater than a diameter of a valley formed between two neighboring ridges of the screw thread of the coupler, and
wherein a diameter of the ball joint head is greater than the diameter of the through-hole.

6. The screw assembly for a spinal implant of claim 5, further comprising a first provisional coupling screw thread formed along an inner circumference surface of the through-hole.

7. The screw assembly for a spinal implant of claim 5, wherein the ball joint head comprises:
a circular flat surface obtained by flatly cutting an upper part of the ball joint head;
a first horizontal bumping pattern having repetitive ring-shaped bumps having a same center from the flat surface to a lower part of the ball joint head; and
a first vertical bumping pattern having repetitive bumps both ends of each of which are connected to an edge of the flat surface and a lower end of the ball joint head and having a grid shape to be perpendicular to the first horizontal bumping pattern,
wherein the first horizontal bumping pattern and the first vertical bumping pattern are coupled with the fourth unit to restrict a rotation of the ball joint head.

8. The screw assembly for a spinal implant of claim 5, wherein the ball joint head comprises:
a bowl-shaped supporting part forming a portion of a sphere having a first radius from a center thereof, wherein an upper surface of the supporting part is flat, a whole or part of a lower surface of the supporting part is positioned in the first unit, and the coupler is formed from the lower surface of the supporting part; and
a rotational part having a same center as the supporting part and forming a portion of a sphere having a second radius smaller than the first radius from the center, wherein a bottom surface of the rotational part contacts and abuts a center of the upper surface of the supporting part to be integrated into the supporting part.

9. The screw assembly for a spinal implant of claim 5, wherein the second unit further comprises a wire guide path linearly passing through a center of each of the ball joint head and the coupler and having a predetermined diameter, and
wherein a medical wire, a bone cement, a bone substitute, or a bone powder is put into the wire guide path.

10. The screw assembly for a spinal implant of claim 9, wherein the second unit further comprises one or more cutout slots formed by cutting to face each other from one end of the coupler to the ball joint head, communicating with the wire guide path.

11. The screw assembly for a spinal implant of claim 5, wherein a screw part of the second unit comprises a screw thread shaped as an unangular, rounded curve,
wherein the screw thread is configured so that each upper surface of the screw thread is inclined upward with respect to a first virtual line passing through a center of the second unit along an upper-lower, longitudinal direction of the second unit, and each lower surface of the screw thread is inclined upward with respect to the first virtual line, or
so that each upper surface of the screw thread is inclined upward with respect to a third virtual line perpendicular to the first virtual line, and each lower surface of the screw thread is inclined upward with respect to the third virtual line.

12. The screw assembly for a spinal implant of claim 5, wherein the valley has one of an unangular, rounded curve shape corresponding to the screw thread, a straight line shape parallel to a first virtual line passing through a center along an upper-lower, longitudinal direction of the second unit, and a shape where both ends of the straight line are not angled and rounded.

13. The screw assembly for a spinal implant of claim 5, wherein only a portion of the screw thread of the coupler spaced apart from the ball joint head is configured to have an unangular, rounded shape.

14. The screw assembly for a spinal implant of claim 1, wherein the pressure cap comprises:
a cap contacting part having an outer circumference surface contacting and fastened to an inner circumference surface of the first unit including the inner space and shaped as a ring to be penetrated from top and bottom;
a cap lower part extending downward along a lower edge of the cap contacting part and comprising a pressing groove inside a bottom of the cap lower part, corresponding to an outer surface of an upper portion of the ball joint head;
a plurality of second horizontal bumping patterns formed along a direction of the pressing groove, corresponding to the first horizontal bumping pattern having ring-shaped repetitive bumps having a same center from a center of an upper end of the ball joint head to a lower end thereof; and
a second vertical bumping pattern having repetitive straight line-shaped bumps in a grid-shape to be perpendicular to the second horizontal bumping patterns on the pressing groove of the cap lower part.

15. The screw assembly for a spinal implant of claim 1, comprising a first screw part shaped as an unangular, rounded screw, formed on an outer circumference surface of the third unit,
wherein the first screw part is coupled with a second screw part formed along an inner circumference surface of an upper portion of the inner space of the first unit,
wherein a screw thread included in the first screw part has any one of a configuration in which each upper surface of the screw thread is inclined upward with respect to a first virtual line passing through a center of the first unit along an upper-lower, longitudinal direction of the first unit and each lower surface of the screw thread is inclined upward with respect to the first virtual line,
a configuration in which each upper surface of the screw thread is inclined upward with respect to the first virtual line and each lower surface of the screw thread is declined downward with respect to the first virtual line, a configuration in which each upper surface of the screw thread is inclined upward with respect to the first virtual line and each lower surface of the screw thread is perpendicular to the first virtual line, a configuration in which each upper surface of the screw thread is perpendicular to the first virtual line and each lower surface of the screw thread is inclined upward with respect to the first virtual line, a configuration in which each upper surface of the screw thread is perpendicular to the first virtual line and each lower surface of the screw thread is declined downward with respect to the first virtual line, and a configuration in which each upper surface of the screw thread is perpendicular to the first virtual line and each lower surface of the screw thread is perpendicular to the first virtual line.

16. The screw assembly for a spinal implant of claim 1, comprising a first screw shaped as an unangular, rounded screw, formed on an outer circumference surface of the third unit, wherein the first screw is coupled with a second screw formed along an inner circumference of an upper side of the inner space of the first unit, wherein a second virtual line is defined to be perpendicular to a first virtual line passing through a center of the first unit along an upper-lower longitudinal direction of the first unit, and wherein an angle between the second virtual line and each upper surface of the screw thread included in the first screw, inclined with respect to the second virtual line is the same or different from an angle between the second virtual line and each lower surface of the screw thread.

* * * * *